US010495642B2

(12) United States Patent
Shastri et al.

(10) Patent No.: US 10,495,642 B2
(45) Date of Patent: Dec. 3, 2019

(54) INHIBITORS OF PROTEINS SPECIFIC FOR THE SECRETOME OF A CHONDROCYTE FOR USE IN THE TREATMENT OF BREAST CANCER METASTASIS

(71) Applicant: ALBERT-LUDWIGS-UNIVERSITÄT FREIBURG, Freiburg (DE)

(72) Inventors: Prasad Shastri, Freiburg (DE); Jon Christensen, Freiburg (DE); Xavier Lucas, Freiburg (DE); Stefan Günther, Freiburg (DE)

(73) Assignee: ALBERT-LUDWIGS-UNIVERSITÄT FREIBURG, Freiburg (DE)

( * ) Notice: Subject to any disclaimer, the term of this patent is extended or adjusted under 35 U.S.C. 154(b) by 0 days.

(21) Appl. No.: 14/786,099

(22) PCT Filed: Apr. 23, 2014

(86) PCT No.: PCT/EP2014/058264

§ 371 (c)(1),
(2) Date: Oct. 21, 2015

(87) PCT Pub. No.: WO2014/173967

PCT Pub. Date: Oct. 30, 2014

(65) Prior Publication Data

US 2016/0069882 A1 Mar. 10, 2016

Related U.S. Application Data

(60) Provisional application No. 61/815,041, filed on Apr. 23, 2013.

(30) Foreign Application Priority Data

Apr. 23, 2013 (EP) .................................... 13164922

(51) Int. Cl.

| | |
|---|---|
| ***G01N 33/53*** | (2006.01) |
| ***G01N 33/567*** | (2006.01) |
| ***G01N 33/574*** | (2006.01) |
| ***A61K 38/10*** | (2006.01) |
| ***A61K 38/04*** | (2006.01) |
| ***C07K 5/00*** | (2006.01) |
| ***C07K 7/00*** | (2006.01) |
| ***C07K 16/00*** | (2006.01) |
| ***C07K 17/00*** | (2006.01) |
| ***G01N 33/68*** | (2006.01) |
| ***C07K 7/08*** | (2006.01) |
| *A61K 38/00* | (2006.01) |

(52) U.S. Cl.

CPC ....... *G01N 33/57415* (2013.01); *A61K 38/10* (2013.01); *C07K 7/08* (2013.01); *G01N 33/574* (2013.01); *G01N 33/68* (2013.01); *A61K 38/00* (2013.01); *G01N 2333/522* (2013.01); *G01N 2333/5412* (2013.01); *G01N 2333/5418* (2013.01); *G01N 2333/5421* (2013.01); *G01N 2333/5428* (2013.01); *G01N 2500/04* (2013.01)

(58) Field of Classification Search

None

See application file for complete search history.

(56) References Cited

U.S. PATENT DOCUMENTS

| | | | | |
|---|---|---|---|---|
| 6,410,268 | B1 | 6/2002 | Ni et al. | |
| 6,645,491 | B1 | 11/2003 | Oldham et al. | |
| 2007/0105133 | A1 * | 5/2007 | Clarke ................. | C12N 5/0693 435/6.12 |
| 2008/0206766 | A1 | 8/2008 | Macoska | |
| 2008/0262203 | A1 | 10/2008 | Clegg et al. | |
| 2011/0105724 | A1 | 5/2011 | Clegg et al. | |

OTHER PUBLICATIONS

Calamia et al., Arthritis Res. Ther. 14:1-12 (2012).*

Smith et al., Chem. Rev. 97:391-410 (1997).*

Christensen et al., "Tumor metastasis targets in bone. A novel strategy to inhibit breast cancer metastases to bone," available online at http://www.campus-technologies.de/wp-content/uploads/TO_ZEE20130417_breast_cancer_targets_bone.pdf, 2 pages (first available Apr. 17, 2013).*

De Ceuninck, Frédéric et al., "The inflammatory side of human chondrocytes unveiled by antibody microarrays," *Biochemical and Biophysical Research Communications*, 2004, 323:960-969.

Halpern, Jennifer L. et al., "Mesenchymal stem cells promote mammary cancer cell migration in vitro via the CXCR2 receptor," *Cancer Letters*, 2011, 308:91-99.

Hsu, Y-L et al., "Breast tumor-associated osteoblast-derived CXCL5 increases cancer progression by ERK/MSK1/Elk-1/Snail signaling pathway," *Oncogene*, 2013, 32:4436-4447.

* cited by examiner

*Primary Examiner* — James H Alstrum-Acevedo
*Assistant Examiner* — Thea D' Ambrosio
(74) *Attorney, Agent, or Firm* — Saliwanchik, Lloyd & Eisenschenk

(57) ABSTRACT

The present invention relates to a method for identifying inhibitors of breast cancer metastasis based on a screening with proteins that are specific for the secretome of a chondrocyte, preferably cytokines and/or chemokines. The ligands as identified lead to a decrease of the migration and/or a re-differentiation of a breast cancer cell and/or a reduction of the number and/or size of breast cancer metastases. The present invention further relates to a method for detecting breast cancer metastasis, comprising the step of detecting at least one protein that is specific for the secretome of a chondrocyte, and for methods for treating and/or preventing breast cancer metastasis in a patient in need thereof, comprising the step of administering an effective amount of at least one ligand for one protein that is specific for the secretome of a chondrocyte to said patient in need thereof.

5 Claims, 10 Drawing Sheets

Figure 5:
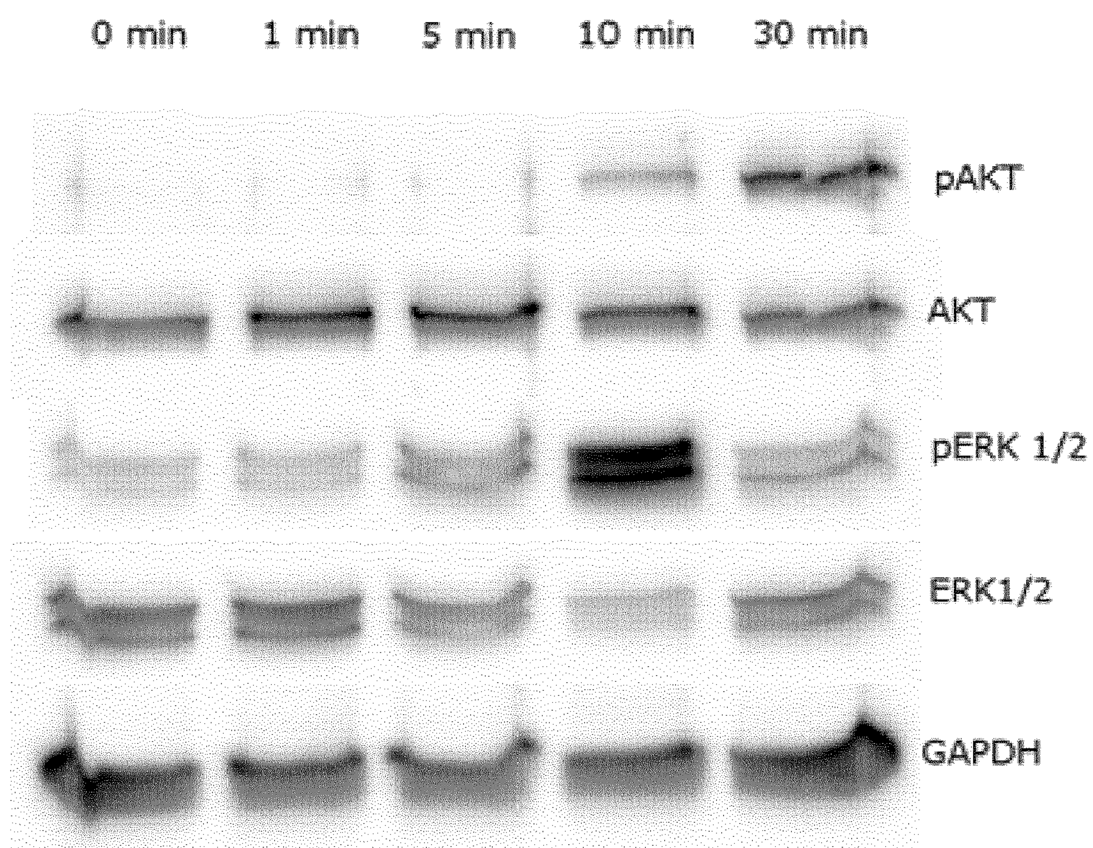

Specification includes a Sequence Listing.

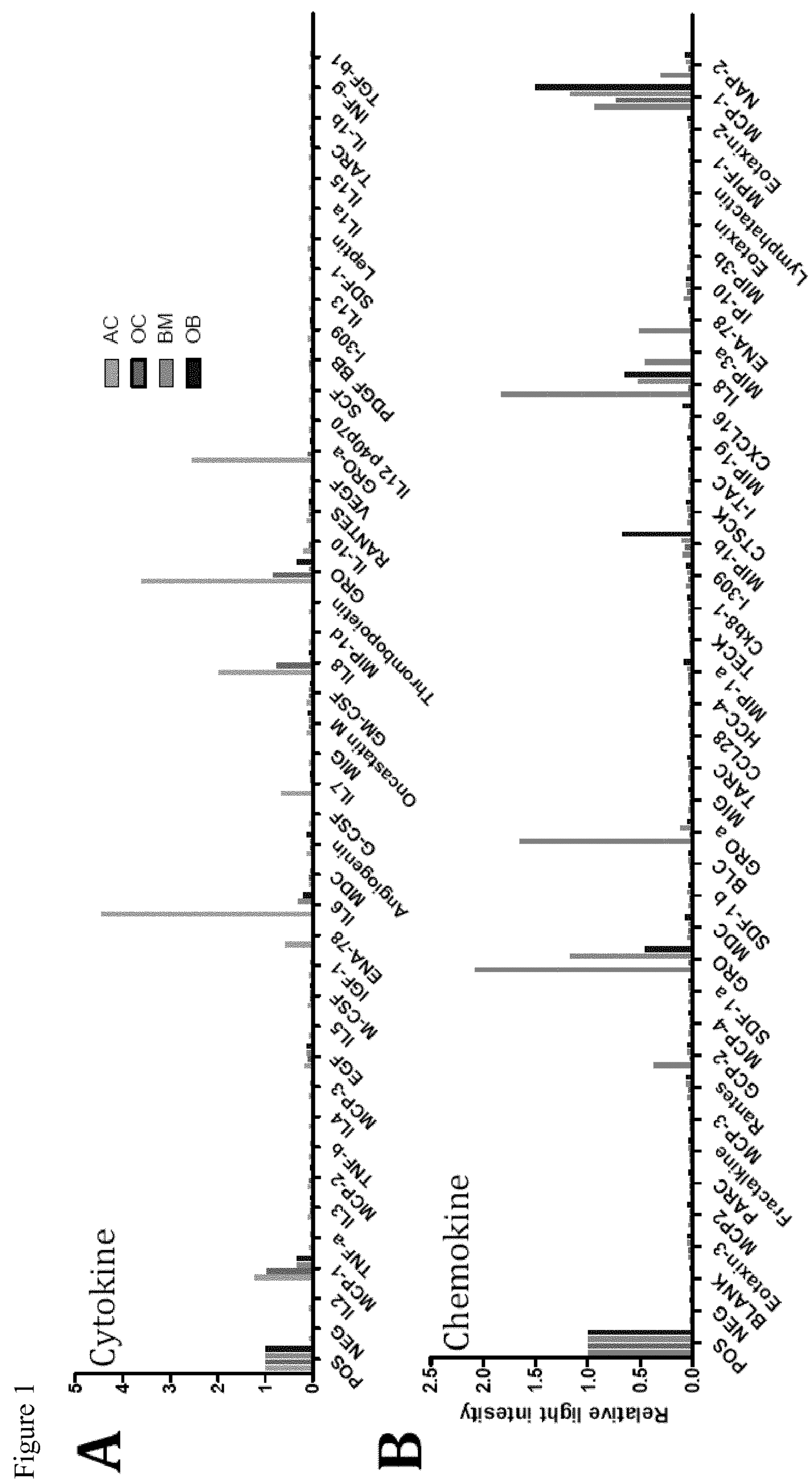
Figure 1
A
Cytokine
AC
OC
BM
OB
0
1
2
3
4
5
POS
NEG
IL2
MCP-1
TNF-a
IL3
MCP-2
TNF-b
IL4
MCP-3
EGF
IL5
M-CSF
IGF-1
ENA-78
IL6
MDC
Angiogenin
G-CSF
IL7
MIG
Oncostatin M
GM-CSF
IL8
MIP-1d
Thrombopoietin
GRO
IL-10
RANTES
VEGF
GRO-a
IL12 p40p70
SCF
PDGF BB
I-309
IL13
SDF-1
Leptin
IL1a
IL15
TARC
IL-1b
INF-g
TGF-b1
B
Chemokine
Relative light intesity
0.0
0.5
1.0
1.5
2.0
2.5
POS
NEG
BLANK
Eotaxin-3
MCP2
PARC
Fractalkine
MCP-3
Rantes
GCP-2
MCP-4
SDF-1 a
GRO
MDC
SDF-1 b
BLC
GRO a
MIG
TARC
CCL28
HCC-4
MIP-1 a
TECK
Ckb8-1
I-309
MIP-1b
CTSCK
I-TAC
MIP-1g
CXCL16
IL8
MIP-3a
ENA-78
IP-10
MIP-3b
Eotaxin
Lymphatactin
MPIF-1
Eotaxin-2
MCP-1
NAP-2

Figure 2
A
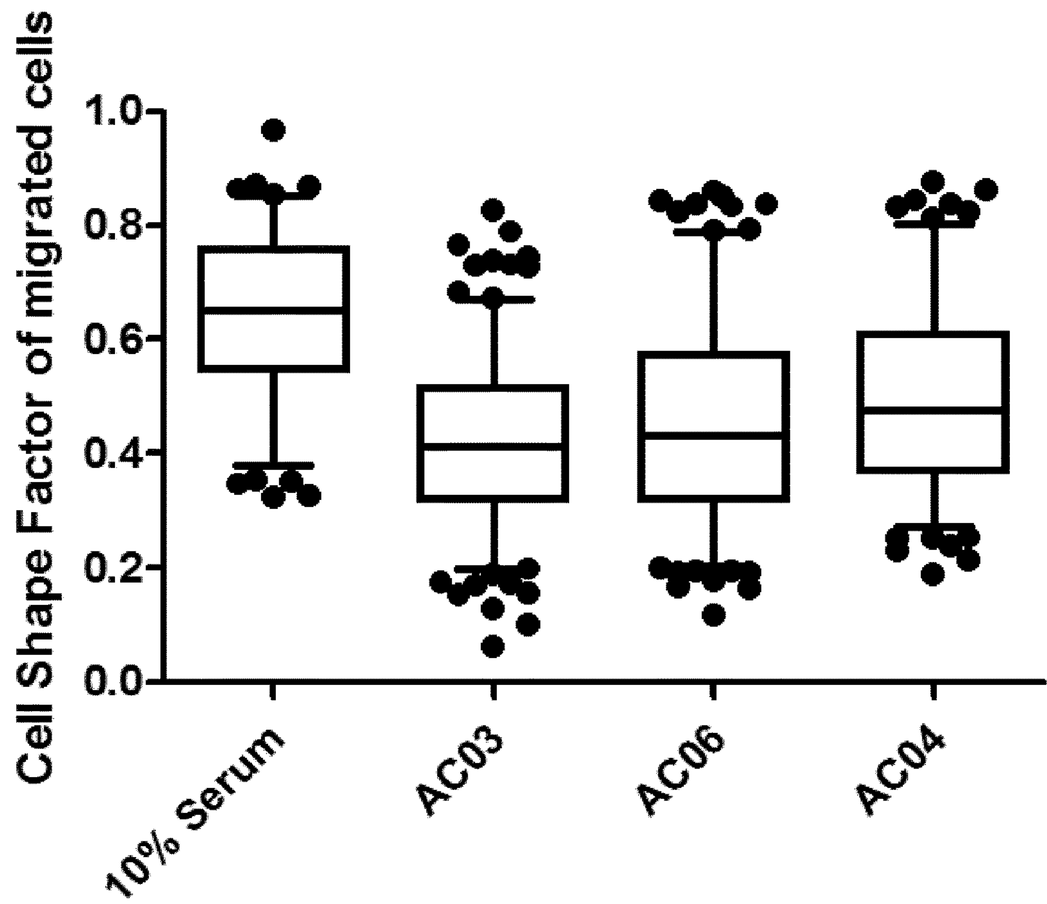
B
10% Serum AC03
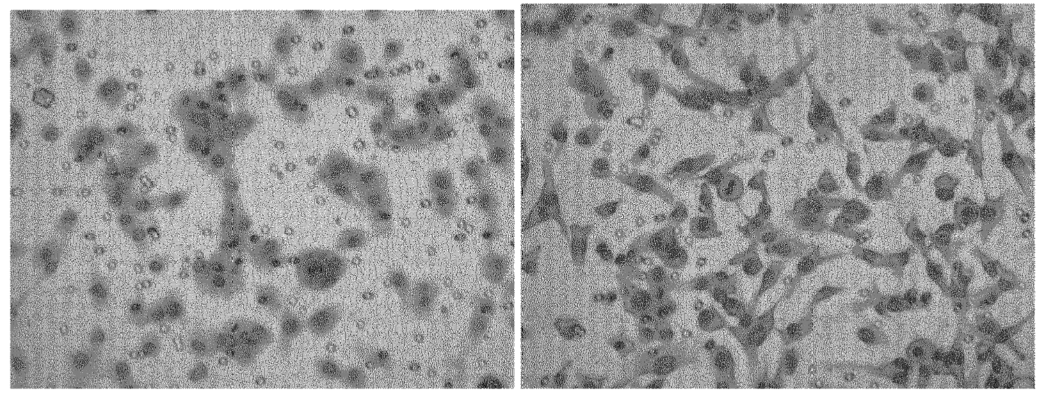

Figure 3
A)
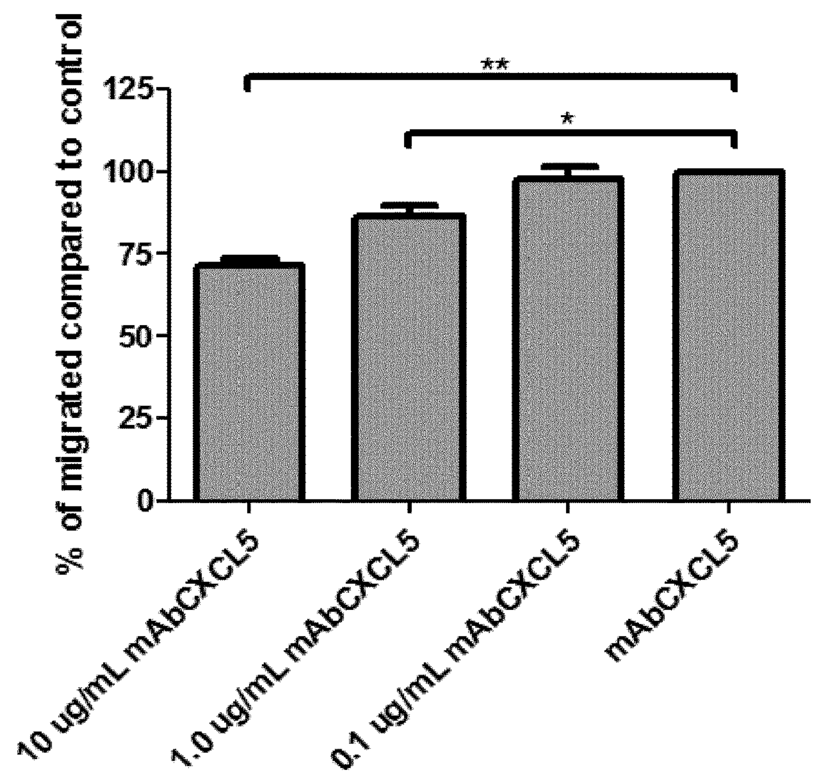
B)
AC03 0.1mg/mL mAbCXCL5
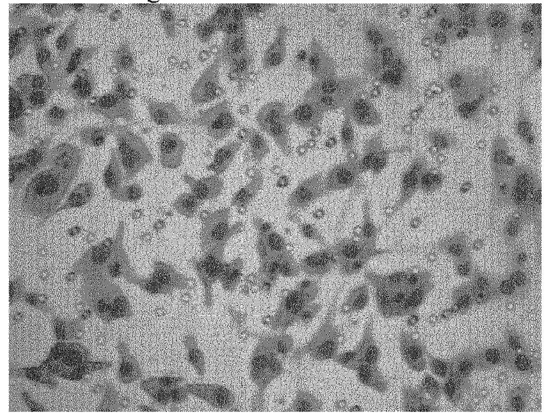
AC03 10mg/mL mAbCXCL5
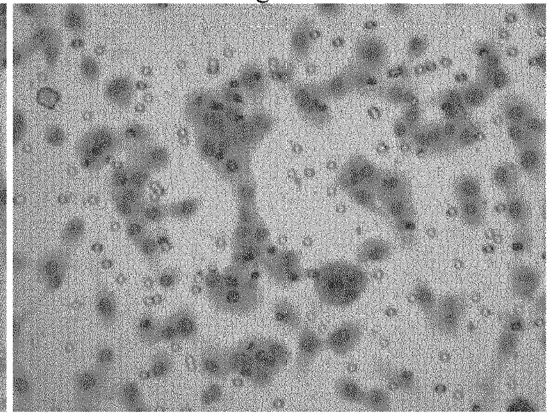

Figure 4
A) 001417C
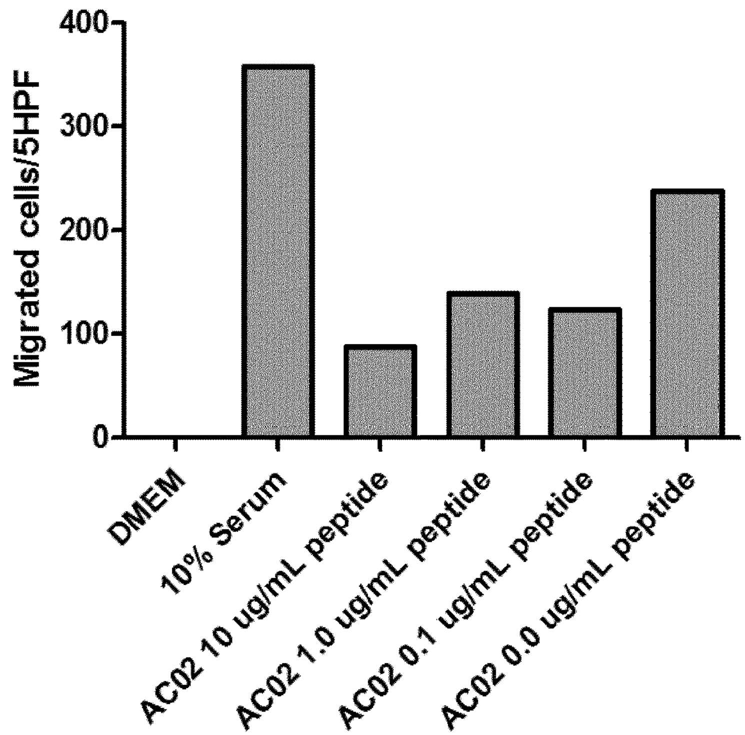
B) 001418C
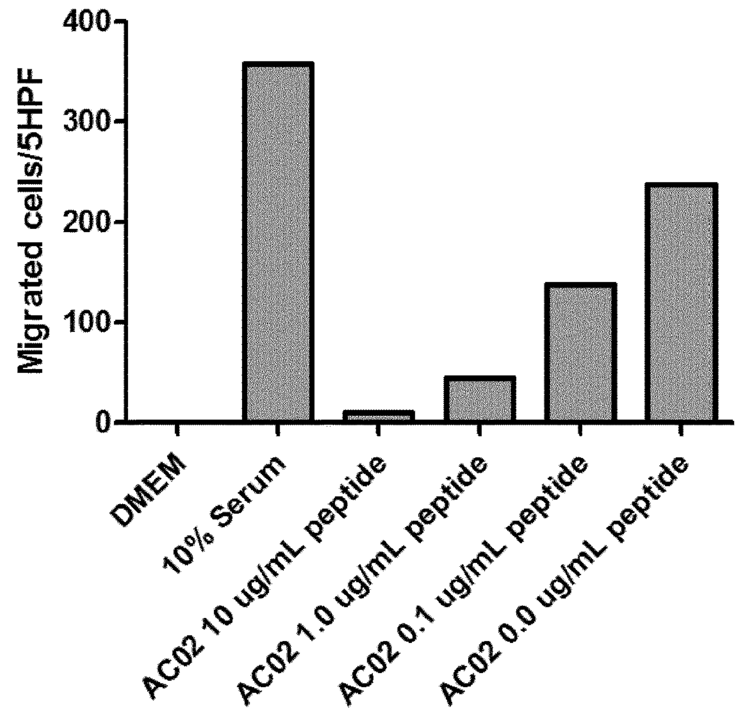

Figure 7

MSLLSSRAARVPGPSSSLCALLVLLLLLTQPGPIASAGPAAAVLRELRCVCLQTTQGVHPKM
ISNLQVFAIGPQCSKVEVVASLKNGKEICLDPEAPFLKKVIQKILDGGNKEN

A
% of migrated cells compared to control
125
100
75
50
25
0
10
1.0
0.1
0.0
Inhibitory Ab CXCL5 [ug/mL]
B
% of migrated compared to control
125
100
75
50
25
0
10
0.0
Inhibitory Ab CXCL5 [ug/mL]
C
% of migrated cells compared to control
125
100
75
50
25
0
10
1.0
0.1
0.0

INHIBITORS OF PROTEINS SPECIFIC FOR THE SECRETOME OF A CHONDROCYTE FOR USE IN THE TREATMENT OF BREAST CANCER METASTASIS

CROSS REFERENCE TO RELATED APPLICATIONS

This application is a National Stage Application of International Application Number PCT/EP2014/058264, filed Apr. 23, 2014; which claims the benefit of U.S. Provisional Application No. 61/815,041, filed Apr. 23, 2013, and European Application No. 13164922.0, filed Apr. 23, 2013; all of which are incorporated herein by reference in their entirety.

The Sequence Listing for this application is labeled "SEQ-9-23-15.TXT", which was created on Sep. 23, 2015, and is 2 KB. The entire content is incorporated herein by reference in its entirety.

The present invention relates to a method for identifying inhibitors of breast cancer metastasis based on a screening with proteins that are specific for the secretome of a chondrocyte, preferably cytokines and/or chemokines. The ligands as identified lead to a decrease of the migration and/or a re-differentiation of a breast cancer cell and/or a reduction of the number and/or size of breast cancer metastases. The present invention further relates to a method for detecting breast cancer metastasis, comprising the step of detecting at least one protein that is specific for the secretome of a chondrocyte, and for methods for treating and/or preventing breast cancer metastasis in a patient in need thereof, comprising the step of administering an effective amount of at least one ligand for one protein that is specific for the secretome of a chondrocyte to said patient in need thereof.

BACKGROUND OF THE INVENTION

Secreted proteins are involved in a variety of physiological processes, including cell signaling and matrix remodeling, but are also integral to invasion and metastasis of malignant cells (Pavlou, Maria P.; Diamandis, Eleftherios P. (2010). "The cancer cell secretome: A good source for discovering biomarkers?". Journal of Proteomics 73 (10): 1896-906).

The secretome is defined as the bulk of peptides, proteins, growth factors, cytokines and other active substances produced and secreted by cells. Secretomics has thus been especially important in the discovery of biomarkers for cancer.

The two main biological sources for cancer secretomics are cancer cell line supernatants and proximal biological fluids, the fluids in contact with a tumor. Cancer cell line supernatant is an attractive source of secreted proteins, but it is unclear whether a cell line secretome is a good representation of an actual tumor in its specific microenvironment and a standardized cell line is not illustrative of the heterogeneity of a real tumor (Karagiannis, George S.; Pavlou, Maria P.; Diamandis, Eleftherios P. (2010). "Cancer secretomics reveal pathophysiological pathways in cancer molecular oncology". Molecular Oncology 4 (6): 496-510). Using secretomic analysis of prostate cell lines, one study was able to discover multiple proteins found in higher levels in the serum of cancer patients than in healthy controls (Makridakis, Manousos; Vlahou, Antonia (2010). "Secretome proteomics for discovery of cancer biomarkers". Journal of Proteomics 73 (12): 2291-305.).

There is also a great need for biomarkers for the detection of breast cancer—currently biomarkers only exist for monitoring later stages of cancer. Secretomic analysis of breast cancer cell lines led to the discovery of the protein ALCAM as a new biomarker with promising diagnostic potential (Makridakis, Manousos; Vlahou, Antonia (2010). "Secretome proteomics for discovery of cancer biomarkers". Journal of Proteomics 73 (12): 2291-305).

Metastasis, the major cause of death for cancer patients, is a complex and multistep process in which secondary cancers are formed in other nonadjacent organs. The development of metastasis includes several steps that consist of cellular transformation and abnormal growth, new blood or lymphatic vessels formation, dissemination of tumor cells into the circulation, attachment to the target organs and growth in target sites. The migratory and invasive ability of cancer cells is required in many of these steps, and is therefore associated with metastasis.

In addition to cancerous cells, also "normal" cells, such as, for example, chondrocytes secrete proteins, and thus have a secretome. In cartilage, the majority of the substances secreted by chondrocytes in vivo are extracellular matrix (ECM) components, especially collagen type II and aggrecan. However, there are numbers of other factors that are secreted as well, like epithelial-derived neutrophil-activating peptide (ENA-78), macrophage inflammatory proteins (MIP-1β), epidermal growth factor (EGF), transforming growth factor beta (TGF-β) and tissue inhibitors of metalloproteinases (TIMP1 and TIMP 2) (Polacek M, Bruun J A, Johansen O, Martinez I. Comparative analyses of the secretome from de-differentiated and redifferentiated adult articular chondrocytes. Cartilage 2010; and De Ceuninck F, Dassencourt L, Anract P. The inflammatory side of human chondrocytes unveiled by antibody microarrays. Biochem Biophys Res Commun 2004; 323(3):960-969).

CXCL5 is a small cytokine belonging to the CXC chemokine family that is also known as epithelial-derived neutrophil-activating peptide 78 (ENA-78). It is produced following stimulation of cells with the inflammatory cytokines interleukin-1 or tumor necrosis factor-alpha. CXCL5 is usually associated with bacterial induced inflammation. The gene for CXCL5 is encoded on four exons and is located on human chromosome 4 amongst several other CXC chemokine genes. CXCL5 has been implicated in connective tissue remodeling.

Kuo et al. (in: Kuo P L, Chen Y H, Chen T C, Shen K H, Hsu Y L CXCL5/ENA78 increased cell migration and epithelial-to-mesenchymal transition of hormone-independent prostate cancer by early growth response-1/snail signaling pathway. J Cell Physiol. 2011 May; 226(5):1224-31) describe the analysis of CXCL5/ENA78, which is highly expressed in androgen-independent prostate cancers, and is responsible for cell migration and epithelial-to-mesenchymal transition in two androgen-independent prostate cancer cell lines. Inducement of PC-3 and suggest that inhibition of CXCL5/ENA78-mediated ERK/Egr-1/Snail signaling would an attractive therapeutic target for androgen-independent prostate cancer.

US 2008-0206766 relates to compositions and methods for the detecting, treating, and empirically investigating cellular proliferation disorders and cellular motility disorders. In particular, the present invention provides compositions and methods for using CXCL chemokines (e.g., CXCL1, CXCL5, CXCL6, CXCL12), CXCL receptors (e.g., CXCR1, CXCR2, CXCR4, CXCR7), and/or pathway related compounds (e.g., NF-kappaB, ERK 1/2, ELK-1) in the diagnosis, treatment, and empirical investigation of prostate disorders (e.g., prostate cancer, benign prostatic hypertrophy, prostatitis).

US 2010-004304 describes that chronic inflammation is an important risk factor for the development of cancer. The proinflammatory cytokine IL-6 is implicated in cancer because it is important for the activation of STAT, a key regulator of cancer growth, survival, metastasis, immune evasion and angiogenesis. Increased IL-6 and Stat-3 exists in vitro in pancreatic cancer, malignant melanoma, papillary thyroid cancer, breast cancer, colon cancer, and prostate cancer cells with high basal expression of Toll-like receptor 3 (TLR3) and Wnt5a. IL6/STAT3 activation, mediated by overexpressed TLR3 signaling, appears important in the tumor growth process; it may increase Wnt5a signaling, and be associated with increased cellular growth and migration. Using a novel inhibitor of pathologic TLR3 signaling (5-phenylmethimazole [C10]) they demonstrated decreases in these markers plus suppression of cell growth and migration in human pancreatic cancer, malignant melanoma, papillary thyroid cancer, breast cancer, colon cancer, and prostate cancer cells.

The metastasis of a tumor is the dominant contributor to fatality. In breast and prostate cancer, bone and lung are the primary sites of metastasis. Therefore, the discovery of molecules for therapeutic targets that are unique to the bone or lung environment are critical for the development of new and more efficient treatment regimens.

It is therefore an object of the present invention, to provide new and effective targets and therapeutics based on secretomics for the diagnosis, prevention and/or treatment of metastases of breast cancer ("secondary breast cancer"). Other objects and advantages will become apparent to the person of skill upon studying the following description and the examples of the invention.

According to a first aspect thereof, the object of the present invention is solved by providing a method for identifying inhibitors of breast cancer metastasis, comprising the steps of: a) providing at least one protein that is specific for the secretome of a chondrocyte; b) contacting said at least one protein with at least one putative ligand of said at least one said protein of the secretome, and c) detecting a binding between said at least one putative ligand and said at least one said protein of the secretome.

The term "ligand" in context of the present invention shall be understood in the broadest sense, and specifically shall include compounds that target the cellular/biological/molecular function of the proteins. Of course the term "ligand" also includes any kind of molecule binding to the proteins of interest, and thereby modulating the proteins stability and/or function, such as, for example inhibiting a signaling pathway of at least one protein that is specific for the secretome of a chondrocyte, such as, for example, the PI3K/AKT pathway in case of CXCL5 signaling.

ENA-78 also referred to as CXCL5 is usually associated with bacterial induced inflammation. In the context of the present invention, it was found that this molecule is also secreted by chondrocytes that can produce hyaline cartilage, and that the inhibition of ENA-78 using, for example, both purified monoclonal antibody and peptides obtained through phage display screening can inhibit the migration of cancer cells induced by the cartilage secretome. Thus, the mature chondrocyte secretome provides a preferable environment for breast cancer metastasis formation, through secretion of chemotatic and mitogenic signals. Migration of MDA-MB-231 cells could be inhibited with monoclonal antibodies (mAb) and proliferation of MCF7A cell could be abrogated by PI3K inhibitor (see examples).

Hsu et al. (in: Hsu Y L, Hou M F, Kuo P L, Huang Y F, Tsai E M. Breast tumor-associated osteoblast-derived CXCL5 increases cancer progression by ERK/MSK1/Elk-1/Snail signaling pathway. Oncogene. 2012 Oct. 8 (online)) describe a study that analyzes the soluble factors secreted by breast tumor-associated osteoblasts (TAOBs), which are described to be responsible for promoting cancer progression. They showed that the addition of CXCL5 did not increase cell proliferation in either MCF-7 or MDA-MB-231 cancer cells, but did enhance the migration and invasiveness of MCF-7 and MDA-MB-231 as well as 4T1 cancer cell lines. Treatment of mice by CXCL5 (0.5 mg/kg) increased the metastasis of 4T1 cells. Tumor nodules in various organs (livers, lungs and intestines) of the CXCL5-treated mice were both more numerous and larger than those found in the control group of mice. Finally, treatment of mice by anti-CXCL5 monoclonal antibody inhibited the metastasis of 4T1 cells in 62.5% (5 of 8) of the mice, in comparison with 100% (8 of 8) of the control mice. The tumor nodules in various organs (livers, lungs and intestines) of the CXCL5 antibody-treated mice were far fewer than those found in the control group mice. The authors conclude that CXCL5 may be a major factor enhancing the metastatic ability of breast cancer cells, and that anti-CXCL5 strategies may be used to target metastasis in breast cancer.

Hsu et al. showed that tumor nodules in livers, lungs and intestines of the CXCL5 antibody-treated mice were far fewer than those found in the control group mice, nevertheless, no effect could be seen in ribs (i.e. bones). Furthermore, regarding the cancer cell line 4T1, Pulaski and Ostrand-Rosenberg (in: Mouse 4T1 breast tumor model. Curr Protoc Immunol. 2001 May; Chapter 20: Unit 20.2) describe the 4T1 mammary carcinoma as a transplantable tumor cell line that is highly tumorigenic and invasive and, unlike most tumor models, can spontaneously metastasize from the primary tumor in the mammary gland to multiple distant sites including lymph nodes, blood, liver, lung, brain, and bone. Thus, the progressive spread of 4T1 metastases to the draining lymph nodes and other organs is very similar to that of human mammary cancer. Nevertheless, Hsu et al. did not show bone metastases in the mouse model.

In contrast to Hsu et al., the present invention is based on the surprising finding that the chondrocyte secretome possesses molecules that induce breast cancer cell migration and metastasis. Chondrocytes are markedly different from osteoblasts, and are a critical component of the cartilage and bone environment and play a role in the renewal and repair of fractures. Thus, the present approach represents a hitherto unknown niche in bone for tumor metastasis.

Preferred is a method according to the present invention, wherein said at least one protein that is specific for the secretome of a chondrocyte is selected from the group consisting of cytokines and chemokines, and more preferably selected from the group consisting of CXCL5, human granulocyte chemotactic protein-2 (GCP-2 or CXCL6), macrophage inflammatory protein-3 alpha (MIP-3a or CCL20), neutrophil-activating protein-2 (NAP-2), interleukin-6 (IL-6), interleukin-7 (IL-7), interleukin-8 (IL-8), interleukin-10 (IL-10), and chemokine (C—X—C motif) ligand 1 (CXCL1, GRO-alpha) (hereinafter also designated as "marker", "markers", "gene" or "genes"). Preferred are GCP-2, GRO-a, MIP3a, CXCL5, NAP-2, IL-7, and IL-10.

Particularly preferred is a method according to the present invention, wherein said at least one protein that is specific for the secretome of a chondrocyte is CXCL5. It was surprisingly found in the context of the present invention that a particular region of the protein CXCL5 is suitable for a screening according to the present invention ("pocket", see FIGS. 7 and 8). Therefore, another aspect of the present invention relates to a method according to the present invention, wherein the protein used for screening is CXCL5 and screening is performed in order to identify identifying potential inhibitors of breast cancer metastasis that are ligands of the pocket of CXCL5. Preferably, said screening using CXCL5 is performed with CXCL5 (see SEQ ID No: 3) as a dimer. In the context of said screening and as an example, two peptides comprising (or consisting of) the amino acid sequence selected from ALWPPNLHAWVP (SEQ ID NO: 1) and AHSVSNSDVLGI (SEQ ID NO: 2) were identified that bind to said region. Another aspect of the present invention therefore relates to the CXCL5-related method as described that is used in order to identify potential binding compounds as described herein (e.g. small molecular drugs) that bind to CXCL5 in a similar or the same manner as the peptides comprising (or consisting of) the amino acid sequence selected from ALWPPNLHAWVP (SEQ ID NO: 1) and AHSVSNSDVLGI (SEQ ID NO: 2). Encompassed is also a competitive screening, where the potentially binding compounds competes with one (or both) of the peptides for a binding to CXCL5, and in particular for the region as described.

The term "contacting" in the context of the present invention means any interaction between the potentially binding substance(s) with said at least one protein that is specific for the secretome of a chondrocyte, whereby any of the two components can be independently of each other in a liquid phase, for example in solution, or in suspension or can be bound to a solid phase, for example, in the form of an essentially planar surface or in the form of particles, pearls or the like.

In a preferred embodiment, a multitude of different potentially binding substances are immobilized on a solid surface like, for example, on a compound library chip and said at least one protein that is specific for the secretome of a chondrocyte (or a functional part thereof) is subsequently contacted with such a chip. Then, a binding between said at least one putative ligand and said at least one protein that is specific for the secretome of a chondrocyte is detected.

The above method can be performed simultaneously (i.e. in one screening reaction) or in parallel (in separate screenings) with one or more of said at least one protein that is specific for the secretome of a chondrocyte, and thus several genes can be arranged to be screened as a "panel". Preferred is a panel with all markers, other preferred panels include 2, 3 or more markers. For reasons of handling, the markers can be pre-screened in pooled fractions of compounds (ligands), and then analyzed further in individual reactions. Based on pre-screenings, also panels of the above genes can be combined that show similar binding characteristics. In this way, different panels can be designed for different ligands (or mixtures of ligands). Particularly preferred is a screening with CXCL5 (e.g. as described above) and/or GRO-alpha.

Preferred is a method according to the present invention, wherein said identifying is a screening and takes place in vitro or in vivo.

The gene product employed in a method of the present invention can be a full length protein (marker) or a fragment with N/C-terminal and/or internal deletions. Preferably the fragment is either an N-terminal fragment or a C-terminal fragment comprising the cytoplasmatic region, depending on whether potentially interacting compounds are sought that specifically interact with the N- or C-terminal fragment.

The potentially binding substance, whose binding to the markers is to be measured, can be any chemical substance or any mixture thereof. For example, it can be a substance selected from the group of a peptide library molecule, an aptamer, a combinatory library molecule, a cell extract derived molecule, a small molecular drug, a bacterial metabolite, a phage display molecule, an antibody or fragment thereof, a protein, a protein fragment, and combinations thereof, and preferably a peptide comprising the amino acid sequence selected from ALWPPNLHAWVP (SEQ ID NO: 1) and AHSVSNSDVLGI (SEQ ID NO: 2), an aptamer, and/or an antibody or fragment thereof. In the context of the present invention, a small molecular drug is a low molecular weight (with a maximum weight of approx. of 800 Daltons) organic compound that serves as a ligand. The upper molecular weight limit for a small molecule is approximately 800 Daltons which allows for the possibility to rapidly diffuse across cell membranes so that they can reach intracellular sites of action. In addition, this molecular weight cutoff is a necessary but insufficient condition for oral bioavailability. Preferred is a lower maximum molecular weight of 500 Daltons based on the observation that clinical attrition rates are significantly reduced if the molecular weight is kept below this 500 Dalton limit.

Measuring of binding of the compound to the at least one marker can be carried out either by measuring a marker or label that can be attached either to the protein or to the potentially interacting compound. Suitable markers or labels are known to someone of skill in the art and comprise, for example, fluorescence or radioactive markers. The binding of the two components can, however, also be measured by the change of an electrochemical parameter of the binding compound or of the protein, e.g. a change of the redox properties of either the marker or the binding compound, upon binding. Suitable methods of detecting such changes comprise, for example, potentiometric methods. Further methods for detecting and/or measuring the binding of the two components to each other are known in the art and can without limitation also be used to measure the binding of the potential interacting compound to the at least one marker or fragments thereof.

Then, preferred is a method according to the present invention, further comprising the steps of: d) in case of a binding of said ligand to said at least one protein, detecting, if said binding between said ligand to said at least one protein leads to a decrease of the migration and/or a re-differentiation of a breast cancer cell and/or a reduction of the number and/or size of breast cancer metastases. Methods to detect these effects of the ligand(s) are known to the person of skill, and preferred methods are described in the examples below, and in the literature as cited herein. If a decrease of the migration and/or a re-differentiation of a breast cancer cell and/or a reduction of the number and/or size of breast cancer metastases is detected, the ligand is selected for further analysis and improvement, if required.

Preferred is a method according to the present invention, wherein said identifying is performed with at least two of said proteins simultaneously, or in parallel. Most preferred is an identification based on the markers CXCL5 and/or GRO-alpha.

Further preferred is a method according to the present invention, wherein breast cancer metastases are bone and/or lung metastases.

The method according to the present invention identifies, for example, ligands selected from an inhibitor of the expression, stability and/or biological function of said at least one protein that is specific for the secretome of a chondrocyte. In the context of the present invention, the term "protein that is specific for the secretome of a chondrocyte" relates to secreted molecules that are either uniquely and/or predominantly (i.e. in higher amounts than in other cells) secreted by chondrocytes, when compared with osteoblasts (OBs), osteoclasts (OCs), and/or bone marrow derived stromal cells (BMCs). As examples, for chondrocytes, uniquely secreted are at least GCP-2, GRO-a, MIP3a, CXCL5, NAP-2, IL-7, and IL-10, and predominantly secreted are at least IL-8 and IL-6.

The method according to the present invention also encompasses several rounds of screening in order to detect, if said ligand is active on several breast cancer cell lines, and/or is binding to several markers as described. Also combinations of ligands can be screened jointly or separately, in order to identify suitable combinations of preferably synergistically active combinations of ligands that inhibit the markers.

The thus selected binding compound(s) (ligands) is then in a preferred embodiment modified in a further step. Modification can be effected by a variety of methods known in the art, which include without limitation the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, isopropyl, n-butyl, isobutyl, tert-butyl, n-pentyl or iso-pentyl groups, lower alkenyl groups, preferably having two to five carbon atoms, lower alkynyl groups, preferably having two to five carbon atoms or through the introduction of, for example, a group selected from the group consisting of NH2, NO2, OH, SH, NH, CN, aryl, heteroaryl, COH or COOH group.

The modified binding substances are than individually tested with a method of the present invention, i.e. they are contacted with the markers again, and subsequently binding of the modified compounds to the marker polypeptide is measured. In this step, both the binding per se can be measured and/or the effect on the migration and/or a re-differentiation of a breast cancer cell and/or a reduction of the number and/or size of breast cancer metastases. If needed, the steps of selecting the binding compound, modifying the binding compound, contacting the binding compound with a marker polypeptide and measuring the binding of the modified compounds to the protein can be repeated a third or any given number of times as required. The above described method is also termed "directed evolution", since it involves a multitude of steps including modification and selection, whereby binding compounds are selected in an "evolutionary" process optimizing its capabilities with respect to a particular property, e.g. its binding activity, its ability to activate, inhibit or modulate the activity of the protein.

As mentioned above, all assays as described herein can be performed either in vitro and/or in vivo. Preferred are in vitro assays.

The method according to the present invention can furthermore encompass a step of detecting and/or measuring the sensitivity to an anti-breast cancer treatment using a protein that is specific for the secretome of a chondrocyte in the absence and presence of the ligand as identified according to the present invention (see also below in the context of diagnosis). The results of such a detection and/or measurement can be used either in order to adjust an already begun anti-cancer treatment using a ligand, e.g. by increasing or decreasing the dosage, and/or to determine, whether a resistance against a ligand has already developed or will develop.

Yet another aspect of the present invention then relates to a ligand for at least one protein that is specific for the secretome of a chondrocyte according to the present invention, wherein said ligand is selected from the group of an inhibitor, activator, competitor or modulator of the expression and/or biological function of said at least one protein, and is preferably a substance selected from the group of a peptide library molecule, an aptamer, a combinatory library molecule, a cell extract derived molecule, a small molecular drug, a bacterial metabolite, a phage display molecule, an antibody or fragment thereof, a protein, a protein fragment, and combinations thereof, and preferably a peptide comprising the amino acid sequence selected from ALWPPNLHAWVP (SEQ ID NO: 1) and AHSVSNSDVLGI (SEQ ID NO: 2), an aptamer, and/or an antibody or fragment thereof. Preferably, said antibody is a human, humanized, mouse or chimeric antibody. Further preferred is a ligand that binds to CXCL5 in a similar or the same manner (e.g. in the same pocket as described herein) as the peptides comprising (or consisting of) the amino acid sequence selected from ALWPPNLHAWVP (SEQ ID NO: 1) and AHSVSNSDVLGI (SEQ ID NO: 2).

As mentioned, preferred is a ligand that is an inhibitor of the expression and/or biological function of said at least one protein. More preferred is a ligand that is an inhibitor of the expression and/or biological function of at least two, three, four or five proteins, even more preferred is a ligand that is an inhibitor of the expression and/or biological function of all proteins as described herein. Of course, the activities and/or affinities of a chosen ligand with respect to the different proteins can vary between markers and ligands.

The term "inhibitor" includes any molecule interfering with the expression and/or function of the above proteins. Preferred are, for example RNAi, based molecules to target protein expression, or molecules binding to the proteins and thereby inhibiting their biological function(s). The latter can be antibodies targeting the proteins, peptides or small molecules, preferably as described and/or screened herein. Specifically preferred are all kinds of cytokine and/or chemokine inhibitors.

Preferred is a ligand according to the present invention, wherein said at least one protein is selected from the group consisting of chemokines, cytokines, CXCL5, GCP-2, MIP-3a, NAP-2, IL-6, IL-7, IL-8, IL-10, GRO, and GRO-a, and preferably CXCL5 and GRO-alpha.

Preferred is the ligand according to the present invention, wherein said ligand is part of a fusion protein, is part of a carrier molecule that optionally comprises at least one anticancer agent, such as, for example, a chemotherapeutic, peptide, small molecule drug, and/or radionucleotide that is conjugated to said ligand, is covalently bound to bisphosphonate or other bone-tissue homing moieties, preferably via a linker that is enzymatically cleaved in the bone-tissue environment, and/or is part of a diagnostic agent that optionally comprises at least one detectable moiety. Preferred is a peptide comprising the amino acid sequence selected from ALWPPNLHAWVP (SEQ ID NO: 1) and AHSVSNSDVLGI (SEQ ID NO: 2) that is coupled or conjugated to a chemotherapeutic substance, such as, for example, at least one anticancer agent, such as, for example, a cytotoxic moiety. The linker can be one that is cleaved by cathepsins and specifically cathepsin-K, or one that is cleaved by MMP-9 and/or MMP-2.

Yet another aspect of the present invention then relates to method for producing a pharmaceutical composition, comprising the steps of: a) optionally, performing a method according to the present invention as above, and b) formulating said at least one ligand as identified, or a ligand according to the present invention as described above, with at least one pharmaceutically acceptable excipient.

Thus, in a further embodiment of the methods of the present invention, the interacting compound (ligand) identified as outlined above, which may or may not have gone through additional rounds of modification and selection, is admixed with suitable auxiliary substances and/or additives. Such substances comprise pharmacological acceptable substances, which increase the stability, solubility, biocompatibility, or biological half-life of the interacting compound or comprise substances or materials, which have to be included for certain routs of application like, for example, intravenous solution, tablets, injectables, sprays, band-aids or pills.

Carriers, excipients and strategies to formulate a pharmaceutical composition, for example to be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form are well known to the person of skill and described in the respective literature.

Administration of an agent, e.g., a compound can be accomplished by any method which allows the agent to reach the target cells, such as metastatic breast cancer cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

Yet another aspect of the present invention is directed at a pharmaceutical composition for treating or preventing breast cancer metastasis, obtainable by a method according to the invention as above. Another aspect of the present invention then relates to the pharmaceutical composition as above, wherein said pharmaceutical composition further comprises additional pharmaceutically active ingredients, for example, anti-cancer chemotherapeutics. Thus, the ligand according to the invention is for administration in combination with other ligands, and/or chemotherapeutically active substances, such as anti-cancer chemotherapeutics.

Preferred is a pharmaceutical composition according to the present invention, wherein said ligand of the at least one marker is selected from an inhibitor, activator, competitor or modulator of the expression and/or biological function of said at least one marker, and is preferably a substance selected from the group of a peptide library molecule, an aptamer, a combinatory library molecule, a cell extract derived molecule, a small molecular drug, a bacterial metabolite, a phage display molecule, an antibody or fragment thereof, a protein, a protein fragment, and combinations thereof, and preferably a peptide comprising the amino acid sequence selected from ALWPPNLHAWVP (SEQ ID NO: 1) and AHSVSNSDVLGI (SEQ ID NO: 2), an aptamer, and/or an antibody or fragment thereof. Preferably, said antibody is a human, humanized, mouse or chimeric antibody. Further preferred is a ligand that binds to CXCL5 in a similar or the same manner (e.g. in the same pocket as described herein) as the peptides comprising (or consisting of) the amino acid sequence selected from ALWPPNLHAWVP (SEQ ID NO: 1) and AHSVSNSDVLGI (SEQ ID NO: 2).

Further preferred is a pharmaceutical composition according to the present invention, wherein said ligand of the at least one marker is part of a fusion protein, is part of a carrier molecule that optionally comprises at least one anticancer agent, such as, for example, a chemotherapeutic, peptide, small molecule drug, and/or radionucleotide that is conjugated to said ligand, and/or is part of a diagnostic agent that optionally comprises at least one detectable moiety. Preferred is a peptide comprising the amino acid sequence selected from ALWPPNLHAWVP (SEQ ID NO: 1) and AHSVSNSDVLGI (SEQ ID NO: 2) that is coupled or conjugated to a chemotherapeutic substance, such as, for example, at least one anticancer agent, such as, for example, a cytotoxic moiety.

Yet another aspect of the present invention then relates to a ligand for at least one protein that is specific for the secretome of a chondrocyte according to the present invention or the pharmaceutical composition according to the present invention for use in the diagnosis of diseases and/or for use in the prevention and/or treatment of diseases. Preferred is the ligand or the pharmaceutical composition for use according to the present invention, wherein said disease to be prevented and/or treated is selected from breast cancer, breast cancer metastases, in particular breast cancer-derived bone metastases, and breast cancer-derived lung metastases.

Preferred is the ligand for use according to the present invention, wherein said ligand of the at least one marker is selected from an inhibitor, activator, competitor or modulator of the expression and/or biological function of said at least one marker, and is preferably a substance selected from the group of a peptide library molecule, an aptamer, a combinatory library molecule, a cell extract derived molecule, a small molecular drug, a bacterial metabolite, a phage display molecule, an antibody or fragment thereof, a protein, a protein fragment, and combinations thereof, and preferably a peptide comprising the amino acid sequence selected from ALWPPNLHAWVP (SEQ ID NO: 1) and AHSVSNSDVLGI (SEQ ID NO: 2), an aptamer, and/or an antibody or fragment thereof. Preferably, said antibody is a human, humanized, mouse or chimeric antibody. Further preferred is a ligand that binds to CXCL5 in a similar or the same manner (e.g. in the same pocket as described herein) as the peptides comprising (or consisting of) the amino acid sequence selected from ALWPPNLHAWVP (SEQ ID NO: 1) and AHSVSNSDVLGI (SEQ ID NO: 2).

Further preferred is a ligand for use according to the present invention, wherein said ligand of the at least one marker is part of a fusion protein, is part of a carrier molecule that optionally comprises at least one anticancer agent, such as, for example, a chemotherapeutic, peptide, small molecule drug, and/or radionucleotide that is conjugated to said ligand, and/or is part of a diagnostic agent that optionally comprises at least one detectable moiety. Preferred is a peptide comprising the amino acid sequence selected from ALWPPNLHAWVP (SEQ ID NO: 1) and AHSVSNSDVLGI (SEQ ID NO: 2) that is coupled or conjugated to a chemotherapeutic substance, such as, for example, at least one anticancer agent, such as, for example, a cytotoxic moiety.

Further preferred is the ligand for use according to the present invention, wherein said ligand is administered systemically and/or administered locally. Even further preferred is the ligand for use according to the present invention, wherein said ligand is for administration in combination with other chemotherapeutically active substances, such as anti-cancer chemotherapeutics as described above.

Yet another aspect of the present invention then relates to a method for treating or preventing breast cancer metastasis in a patient in need thereof, comprising the step of administering an effective amount of at least one ligand for one protein that is specific for the secretome of a chondrocyte or of a pharmaceutical preparation according to the present invention to said patient in need thereof.

Preferably, an active agent (ligand) is administered in the form of a pharmaceutical composition, such as an antibody, peptide, or a binding compound. Preferably, said patient is a human being or a domesticated animal. Treating is meant to include, e.g., preventing, treating, reducing the symptoms of, or curing the disease or condition. The invention also includes a combination comprising (a) a ligand according to the present invention for a first marker and (b) at least one ligand according to the present invention for a second marker, for use in the treatment/prevention of breast cancer metastasis. Preferred agents (a) and (b) are described in the present application. The combinatorial use of ligands inhibiting the above mentioned proteins yields surprising synergistic results that are translated into new therapeutic uses by the herein disclosed invention.

An "effective amount" is an amount of the ligand(s) as mentioned above that acts on the at least one protein and decreases the migration and/or a re-differentiation of a breast cancer cell and/or a reduction of the number and/or size of breast cancer metastases, and thus alleviates symptoms as found for the disease. Alleviating is meant to include, e.g., preventing, treating, reducing the symptoms of, or curing the disease or condition. Thus, preferred is a method according to the present invention, wherein said administering of said ligand to said at least one protein decreases the migration and/or a re-differentiation of a breast cancer cell and/or reduces the number and/or size of breast cancer metastases. Preferably, said breast cancer metastases to be treated are bone and/or lung metastases.

Preferred is a method according to the present invention, wherein said at least one protein that is specific for the secretome of a chondrocyte is selected from the group consisting of cytokines, chemokines, CXCL5, GCP-2, MIP-3a, NAP-2, IL-6, IL-7, IL-8, IL-10, GRO, and GRO-a.

Preferred is a method according to the present invention, wherein, wherein said ligand is selected from an inhibitor of the expression, stability and/or biological function of said at least one protein, and is preferably selected from a peptide library molecule, an aptamer, a combinatory library molecule, a cell extract derived molecule, a small molecular drug, a bacterial metabolite, a phage display molecule, an antibody or fragment thereof, a protein, a protein fragment, and combinations thereof, and preferably a peptide comprising an amino acid sequence selected from ALWPPNLHAWVP (SEQ ID NO: 1) and AHSVSNSDVLGI (SEQ ID NO: 2), an aptamer, and/or an antibody or fragment thereof. Further preferred is a ligand that binds to CXCL5 in a similar or the same manner (e.g. in the same pocket as described herein) as the peptides comprising (or consisting of) the amino acid sequence selected from ALWPPNLHAWVP (SEQ ID NO: 1) and AHSVSNSDVLGI (SEQ ID NO: 2).

Further preferred is a method according to the present invention, wherein said ligand of the at least one marker is part of a fusion protein, is part of a carrier molecule that optionally comprises at least one anticancer agent, such as, for example, a chemotherapeutic, peptide, small molecule drug, and/or radionucleotide that is conjugated to said ligand, and/or is part of a diagnostic agent that optionally comprises at least one detectable moiety. Preferred is a peptide comprising the amino acid sequence selected from ALWPPNLHAWVP (SEQ ID NO: 1) and AHSVSNSDVLGI (SEQ ID NO: 2) that is coupled or conjugated to a chemotherapeutic substance, such as, for example, at least one anticancer agent, such as, for example, a cytotoxic moiety.

Even further preferred is a method according to the present invention, wherein said ligand is for administration in combination with other chemotherapeutically active substances, such as anti-cancer chemotherapeutics, as described above.

Another aspect of the present invention is based on the fact that bone matrix remodeling occurs throughout the lifetime of an individual. The remodeling of long bone occurs via a process involving endochondral ossification, wherein the formation of a cartilage callus is a necessary first step. Such cartilaginous environment is also associated with healing of micro-fractures. Furthermore, long bones constitute the primary targets of breast cancer metastasis. Chondrocytes and their activities during the formation of cartilage play an essential role in this process.

Interestingly, Ulici et al. (in: Ulici V, Hoenselaar K D, Gillespie J R, Beier F. The PI3K pathway regulates endochondral bone growth through control of hypertrophic chondrocyte differentiation. BMC Dev Biol. 2008 Apr. 11; 8:40) describe an essential role of PI3K signaling in chondrocyte differentiation and as a consequence of this, in the endochondral bone growth process.

Yet another aspect of the present invention then relates to methods of screening for ligands for preventing and/or treating tumor metastasis, in particular in breast cancer, by inhibiting and/or limiting the formation of cartilaginous entities within long bones of a patient, for example, by inhibiting and/or limiting the processes involved in endochondral ossification. The screening can be done in analogy to the methods as described herein, and preferably involves the use of chondrocytes and/or targets chondrocyte-specific functions in the formation of cartilaginous entities in vivo and/or in vitro.

Another aspect of this invention then relates to a method for the prevention and/or treatment of tumor metastasis, in particular in breast cancer, by limiting or inhibiting the formation of cartilaginous entities within long bones in analogy to the methods as described herein. Another aspect of this invention then relates to the development of targeted therapeutics to be directed at and for detecting the cartilaginous moieties within long bones of a patient, for example, by inhibiting and/or limiting or detecting the processes involved in endochondral ossification, again in analogy to the methods, to the ligands and to the pharmaceutical preparations as described herein.

Yet another aspect of the present invention then relates to a method for detecting breast cancer metastasis, comprising the step of detecting at least one protein that is specific for the secretome of a chondrocyte selected from the group consisting of cytokines, chemokines, CXCL5, GCP-2, MIP- 3a, NAP-2, IL-6, IL-7, IL-8, IL-10, GRO, and GRO-a in a biological sample obtained from a subject having primary breast cancer; wherein the presence of said at least one protein that is specific for the secretome of a chondrocyte is indicative for breast cancer metastasis and/or an increased risk for breast cancer metastasis.

Preferred is a method according to the present invention, wherein said detecting comprises detecting of a binding of a ligand according to the present invention, preferably coupled to a detectable moiety as described above. Suitable markers or labels that can be attached either to the protein or to the ligand are known to someone of skill in the art and comprise, for example, fluorescence or radioactive markers. The binding of the two components can, however, also be measured by the change of an electrochemical parameter of the binding compound or of the protein, e.g. a change of the redox properties of either the marker or the binding compound, upon binding. Suitable methods of detecting such changes comprise, for example, potentiometric methods. Further methods for detecting and/or measuring the binding of the two components to each other are known in the art and can without limitation also be used to measure the binding of the potential interacting compound to the at least one marker or fragments thereof.

The results of such a detection and/or measurement can also be used either in order to adjust an already begun anti-cancer treatment using a ligand or a pharmaceutical composition according to the present invention, e.g. by increasing or decreasing the dosage, and/or to determine, whether a resistance against a ligand according to the present invention has already developed or will develop.

Preferred is a method according to the present invention, wherein said metastases are bone and/or lung metastases.

Methods to detect binding are well known to the person of skill and may comprise methods involving cell sorting, marker antibody-based assays, gel analyses, protein or nucleic acid based blots, rtPCR, and/or chip analyses.

Preferred is a method according to the present invention, wherein said sample is selected from a blood, plasma, urine, a sample comprising chondrocytes, and a tissue sample, such as, for example, a biopsy comprising breast, bone, cartilage, lung, liver, brain or tumor tissue.

Another aspect of the present invention then relates to a screening tool for a ligand for at least one protein that is specific for the secretome of a chondrocyte, wherein said tool is a cell which recombinantly expresses at least one product of a gene selected from the group consisting of selected from the group consisting of cytokines, chemokines, CXCL5, GCP-2, MIP-3a, NAP-2, IL-6, IL-7, IL-8, IL-10, GRO, and GRO-a. The expression constructs can be present extrachromosomally or integrated into the chromosome. The marker polypeptide (or part thereof) can be expressed in the form of a fusion protein, for example together with an enzymatically active moiety as reporter-construct, in order to be able to detect the expression product.

The screening tool can be part of a kit, optionally comprising additional compounds and instructions for performing the methods as described herein.

Preferred is the screening tool according to the present invention, wherein said cell is a chondrocyte in a non-human transgenic mammal. Preferred is a transgenic mouse, rat, pig, monkey, goat, cow or sheep. Methods to produce these non-human transgenic mammals are well known to the person of skill in the art.

Similar to the kit including a screening tool according to the present invention, diagnostic kits can be designed that include diagnostic tools, which are cells and/or animals as above. The diagnostic tool can be part of a kit, optionally comprising additional compounds and instructions for performing the methods as described herein.

The following figures, sequences, and examples merely serve to illustrate the invention and should not be construed to restrict the scope of the invention to the particular embodiments of the invention described in the examples. For the purposes of the present invention, all references as cited in the text are hereby incorporated in their entireties.

FIGURES

FIGS. 1A-1B: Analysis of the secretome of chondrocytes for (1A) cytokines and (1B) chemokines (see also tables and 1 and 2).

FIGS. 2A-2B: The chondrocyte secretome induces morphological changes in migrating MBA-MB-231 cells. 2A) cell shape factors of three samples of chondrocytes (AC) after the addition of chondrocyte-conditioned medium. 2B) Photograph of the morphological changes of sample AC03.

FIGS. 3A-3B: The Inhibition of CXCL5/ENA-78 in chondrocyte secretome reverse (rescues) morphology of MDA-MB-231 cells. 3A) reduction of migration of chondrocytes (AC) after the addition of an inhibitor of CXCL5/ENA-78. 3B) Photograph of the morphological changes of sample AC03.

FIGS. 4A-4B: Inhibition of CXCL5/ENA-78 in chondrocyte secretome reduces migration of MDA-MB-231 cells. 4A) Effect of peptide 001417C; 4B) Effect of peptide 001418C.

FIG. 5: Chondrocyte-conditioned medium promotes mitogentic signaling through PI3K/AKT pathway in MCF7A—Western blot showing activation of AKT and ERK1/2 pathway in MCF7A upon treatment with chondrocyte-conditioned medium (AC CM).

Figure 6:
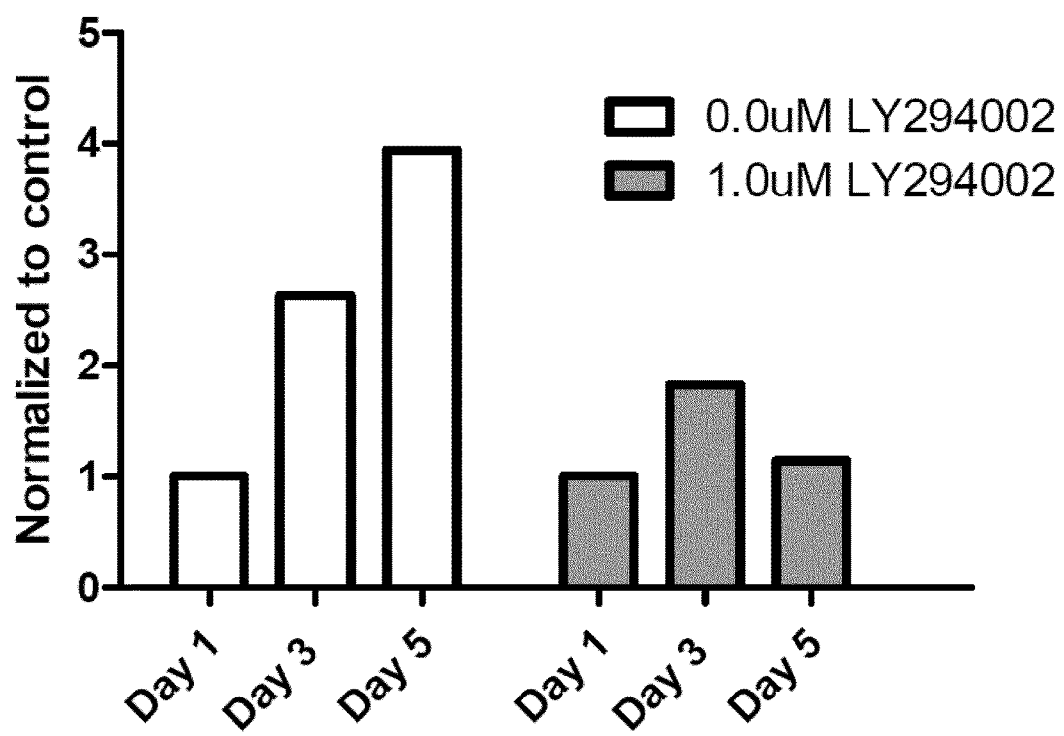

FIG. 6: Inhibition of AC CM induced proliferation in MCF7A using PI3K inhibitors (e.g. LY294002).

FIG. 7: Primary amino acid sequence of CXCL5 (SEQ ID NO: 3). Residues in contact with peptide #1 (SEQ ID NO: 1 at 4 Angstroms) are underlined.

Figure 8:
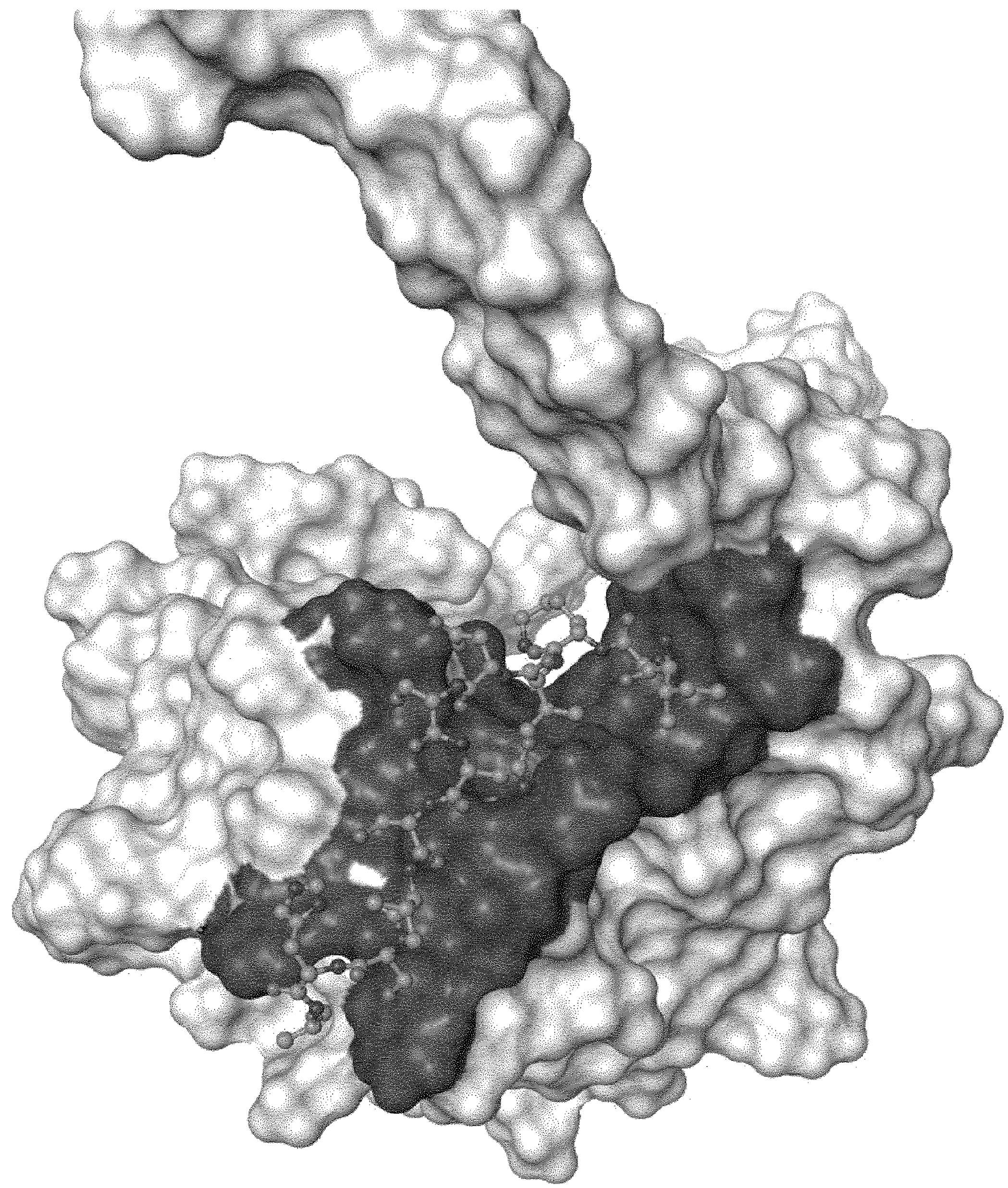

FIG. 8: Screenshot of the CXCL5 surface colored in white and with the region in contact with the peptide #1 (SEQ ID NO: 1) highlighted in gray. Peptide #1, in the proposed binding mode, is shown in balls and sticks.

Figure 9:
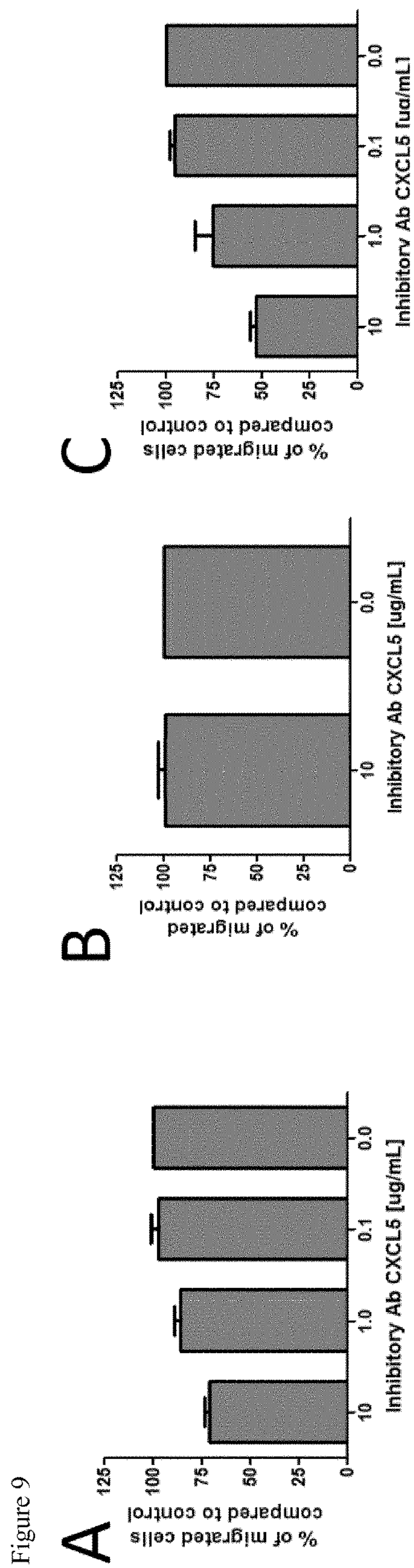
Figure 10:
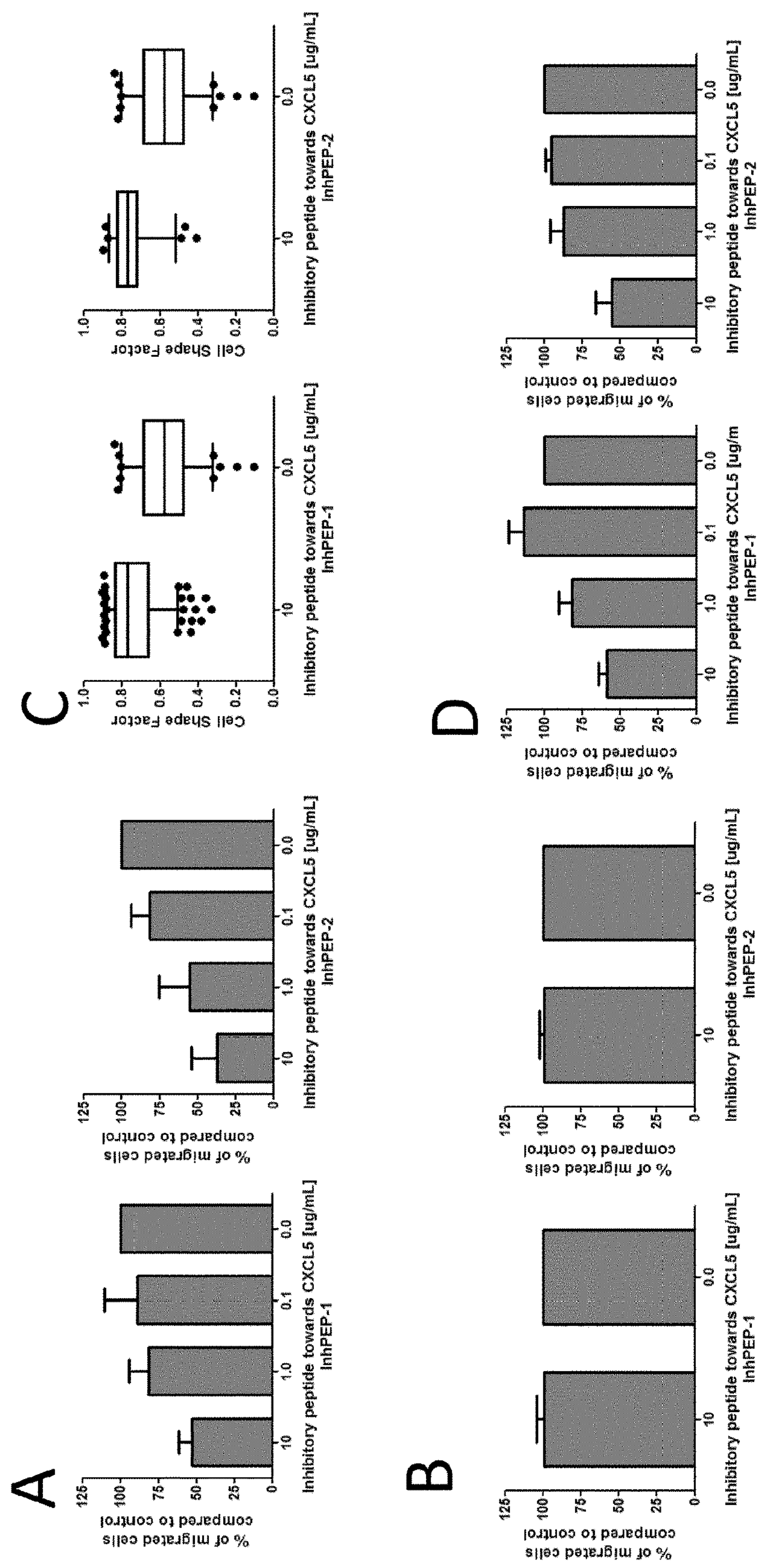

FIGS. 9A-9C: Inhibition data mAB: Inhibition of chondrocyte secreted CXCL5 inhibits migration and invasion of MDA-MB-231 breast cancer cells. (9A) Percent reduction of MDA-MB-231 cells migrating towards chondrocyte conditioned media, with increasing amount of CXCL5 inhibitory antibody (Ab), n=4. (9B) Inhibition of CXCL5 does not reduce the migration of MDA-MB-231 cell when osteoblast conditioned media is used as chemoattractant, n=3. (9C) Filters were coated with Matrigel and MDA-MB-231 cells were allowed to invade through the matrix. Chondrocyte conditioned media was used as chemoattractant supplemented with CXCL5 inhibitory antibody.

FIGS. 10A-10D: Inhibition data InhPep: CXCL5 binding peptides can inhibit migration and invasion of MDA-MB-231 cells towards chondrocyte conditioned media. (10A) Migration of MDA-MB-231 cells towards chondrocyte conditioned media supplemented with CXCL5 binding peptides InhPEP-1 or InhPEP2, n=3. (10B) Migration of MDA-MB-231 cells towards osteoblast conditioned media supplemented CXCL5 binding peptides InhPEP-1 or InhPEP2, n=3. (10C) Cell shape analysis of MDA-MB-231 cells that migrated towards chondrocyte conditioned media supplemented with CXCL5 binding peptides InhPEP-1 or InhPEP2. (10D) Filters were coated with Matrigel and MDA-MB-231 cells were allowed to invade through the matrix. Chondrocyte conditioned media was used as chemoattractant supplemented with CXCL5 binding peptides InhPEP-1 or InhPEP2.

EXAMPLES

The present methods have been performed with CXCL5 as an example, but can be used for other proteins of the secretome of chondrocytes as well, such as, for example GCP-2, MIP-3a, NAP-2, IL-6, IL-7, IL-8, IL-10, GRO, and/or GRO-a.

Cell differentiation: Primary human monocytes, articular chondrocytes, and adipose tissue derived stromal cells were isolated from healthy donors and differentiated into osteoclasts (OC), articular chondrocytes (AC) and osteoblasts (OB) respectively. Cell lines: MDA-MB-231 (MDA), a metastatic, and MCF7A, an epithelial like breast cancer cell line, were used in this study.

Serum free conditioned media: After differentiation, cells were washed 2 times with PBS and incubated with DMEM for 24 hours. After 24 hours, conditioned media was harvested and passed through a 0.45 μm filter.

Migration: MDA-MB-231 cells were serum-starved for 24 hours before testing of the migration. Migration media was plated in the bottom of the well and a transwell insert (8 μm pores) was placed on top. 25.000 cells were seed on top of the filter. After 15 hours, the filters were washed and non-migrated cells were removed. Migrated cells were stained with H&E and counted under a microscope. Numbers were obtained as the average number of 5 random fields per filter.

MTT: Proliferation was measured using MTT assay. Cells were seeded in a 96 well plate. After one day, the medium was changed to the appropriate medium. At the time for analysis, 5 μL MTT (10 μg/mL) was added to each well and incubated for 4 hours. Afterwards, the solution was removed, and DMSO was added. The absorbance was measured at 550 nm.

Cell shape: Cell shape was analyzed using the program imageJ.

Antibody array: The detection of proteins in the secretome was done using commercially available membrane antibody arrays from RayBiotech. CM was incubated with antibody arrays against chemokines and cytokines and detected using chemiluminescence.

Phage display: 12 amino acid binding peptides towards CXCL5 were identified using a commercial phage display system from New England Biosystems.

Intracellular Ca2+ imaging was done using Fura-2. Cells were incubated with Fura-2 and the ratio between fluorescence intensities at 340 nm and 380 nm was measured and plotted.

Results

Using the above methods, first, a cytokine pattern was identified for cytokines that are specific (unique) (in bold) for the secretome of chondocytes according to the following table 1 (see also FIGS. 1A-1B). Predominant cytokines as identified are indicated in italics. POS=positive control; NEG=negative control, BMC=Bone marrow derived stromal cells

| Name | Chondrocytes Norm | BMC | Osteo-blasts | Osteo-clasts |
|---|---|---|---|---|
| POS | 1 | 1 | 1 | 1 |
| NEG | 0.066679 | 0.017539 | 0.027469 | 0.020553 |
| IL2 | 0.06822 | 0.029074 | 0.027572 | 0.022438 |
| MCP-1 | 1.217602 | 0.3431 | 0.339299 | 0.963559 |
| TNF-a | 0.083163 | 0.046156 | 0.036696 | 0.034415 |
| IL3 | 0.109001 | 0.057641 | 0.053618 | 0.059465 |
| MCP-2 | 0.114293 | 0.040159 | 0.044784 | 0.077262 |
| TNF-b | 0.080495 | 0.055858 | 0.039132 | 0.036499 |
| IL4 | 0.065596 | 0.026211 | 0.027045 | 0.020462 |
| MCP-3 | 0.069777 | 0.041931 | 0.036496 | 0.02842 |
| EGF | 0.173708 | 0.145263 | 0.124084 | 0.10602 |
| IL5 | 0.070889 | 0.028318 | 0.027409 | 0.020449 |
| M-CSF | 0.094147 | 0.054951 | 0.043839 | 0.053754 |
| IGF-1 | 0.069955 | 0.046404 | 0.039877 | 0.030477 |
| **ENA-78** | **0.580272** | **0.039544** | **0.033606** | **0.026904** |
| **IL6** | **4.458285** | **0.312157** | **0.210344** | **0.028285** |
| MDC | 0.06951 | 0.044773 | 0.032661 | 0.077925 |
| Angiogenin | 0.130348 | 0.049213 | 0.128664 | 0.053362 |
| G-CSF | 0.073201 | 0.030328 | 0.026645 | 0.020192 |
| **IL7** | **0.674108** | **0.054183** | **0.044566** | **0.021315** |
| MIG | 0.066486 | 0.038226 | 0.031662 | 0.025064 |
| Oncastatin M | 0.122209 | 0.078958 | 0.094876 | 0.068533 |
| GM-CSF | 0.122743 | 0.085959 | 0.062287 | 0.063404 |
| **IL8** | **1.971182** | **0.056809** | **0.067922** | **0.778721** |
| MIP-1d | 0.066842 | 0.031235 | 0.027645 | 0.024996 |
| Thrombopoietin | 0.075069 | 0.040592 | 0.036405 | 0.027825 |
| **GRO** | **3.603709** | **0.069439** | **0.333483** | **0.847619** |
| ***IL-10*** | ***0.193054*** | ***0.033493*** | ***0.030371*** | ***0.062822*** |
| RANTES | 0.11883 | 0.08383 | 0.064541 | 0.066543 |
| VEGF | 0.067953 | 0.045875 | 0.035369 | 0.025091 |
| **GRO-a** | **2.552966** | **0.037847** | **0.0522** | **0.114478** |
| IL12 p40p70 | 0.067642 | 0.042385 | 0.032334 | 0.033116 |
| SCF | 0.073957 | 0.045659 | 0.038223 | 0.0334 |
| PDGF BB | 0.065285 | 0.055458 | 0.045311 | 0.06404 |
| I-309 | 0.093258 | 0.046966 | 0.043567 | 0.038475 |
| IL13 | 0.065819 | 0.026038 | 0.026463 | 0.020016 |
| SDF-1 | 0.068709 | 0.049419 | 0.046384 | 0.040627 |
| Leptin | 0.092324 | 0.052001 | 0.040222 | 0.037338 |
| IL1a | 0.064796 | 0.031397 | 0.031443 | 0.024549 |
| IL15 | 0.075558 | 0.036248 | 0.031916 | 0.021626 |
| TARC | 0.070533 | 0.059218 | 0.04433 | 0.037474 |
| IL-1b | 0.062973 | 0.034325 | 0.034879 | 0.028596 |
| INF-g | 0.067375 | 0.039403 | 0.035133 | 0.027364 |
| TGF-b1 | 0.072089 | 0.054443 | 0.04144 | 0.034063 |

Second, a chemokine pattern was identified for cytokines that are specific (unique) (in bold) for the secretome of chondocytes according to the following table 2. Predominant cytokines as identified are indicated in italics. (see also FIGS. 1A-1B). Abbr. see Table 1.

| Name | Chondrocytes Norm | BMC | Osteo-blasts | Osteo-clasts |
|---|---|---|---|---|
| POS | 1 | 1 | 1 | 1 |
| NEG | 0.02855 | 0.01466 | 0.02252 | 0.02853 |
| Eotaxin-3 | 0.03941 | 0.03665 | 0.05101 | 0.05389 |
| MCP2 | 0.034 | 0.02502 | 0.02885 | 0.04779 |
| PARC | 0.02727 | 0.02446 | 0.02918 | 0.03463 |
| Fractalkine | 0.03062 | 0.02841 | 0.03547 | 0.03988 |
| MCP-3 | 0.032 | 0.02357 | 0.02709 | 0.03633 |
| Rantes | 0.05469 | 0.04292 | 0.05864 | 0.06533 |
| **GCP-2** | **0.376229** | **0.032181** | **0.046655** | **0.044334** |
| MCP-4 | 0.04013 | 0.0235 | 0.02659 | 0.0353 |
| SDF-1 a | 0.04002 | 0.02583 | 0.04274 | 0.0375 |
| **GRO** | **2.08272** | **0.03558** | **1.16742** | **0.45779** |
| MDC | 0.04859 | 0.03593 | 0.04364 | 0.0737 |
| SDF-1 b | 0.03548 | 0.03057 | 0.04493 | 0.04088 |
| BLC | 0.02893 | 0.0263 | 0.0345 | 0.03796 |
| GRO a | 1.657005 | 0.026569 | 0.118857 | 0.047771 |
| MIG | 0.03617 | 0.02547 | 0.0331 | 0.0362 |
| TARC | 0.03788 | 0.02988 | 0.03977 | 0.04457 |
| CCL28 | 0.02845 | 0.02467 | 0.02448 | 0.03463 |
| HCC-4 | 0.03687 | 0.02371 | 0.03106 | 0.03831 |

-continued

| Name | Chondrocytes Norm | BMC | Osteo-blasts | Osteo-clasts |
|---|---|---|---|---|
| MIP-1 a | 0.03908 | 0.03419 | 0.04794 | 0.08943 |
| TECK | 0.02784 | 0.02461 | 0.03232 | 0.03341 |
| Ckb8-1 | 0.04352 | 0.03516 | 0.04026 | 0.04801 |
| I-309 | 0.06397 | 0.04242 | 0.04853 | 0.0584 |
| MIP-1b | 0.09124 | 0.0734 | 0.10668 | 0.67802 |
| CTSCK | 0.05321 | 0.04033 | 0.05319 | 0.06158 |
| I-TAC | 0.03436 | 0.03131 | 0.03593 | 0.04165 |
| MIP-1g | 0.03116 | 0.02555 | 0.02649 | 0.04729 |
| CXCL16 | 0.03417 | 0.02506 | 0.0304 | 0.09064 |
| ***IL8*** | ***1.830818*** | ***0.041717*** | ***0.522773*** | ***0.649224*** |
| **MIP-3a** | **0.452969** | **0.022053** | **0.024229** | **0.029753** |
| **ENA-78** | **0.511243** | **0.023615** | **0.029447** | **0.03794** |
| IP-10 | 0.08671 | 0.04606 | 0.05728 | 0.06331 |
| MIP-3b | 0.04593 | 0.02595 | 0.02763 | 0.03415 |
| Eotaxin | 0.02944 | 0.02283 | 0.03761 | 0.03288 |
| Lymphatactin | 0.0355 | 0.03193 | 0.04076 | 0.03973 |
| MPIF-1 | 0.02872 | 0.0238 | 0.02756 | 0.03984 |
| Eotaxin-2 | 0.03329 | 0.02705 | 0.03645 | 0.05566 |
| MCP-1 | 0.94123 | 0.72813 | 1.17109 | 1.49859 |
| **NAP-2** | **0.300804** | **0.038889** | **0.065753** | **0.080037** |

As can be seen examples, for chondrocytes, uniquely secreted are at least GCP-2, GRO-a, MIP3a, CXCL5, NAP-2, IL-7, and IL-10, and predominantly secreted are at least IL-8 and IL-6.

Then, also using the above methods, the migration of MDA-MB231 breast cancer cells in the presence of the chondrocyte secretome has been severely inhibited by blocking the signaling of ENA-78 (CXCL5) using monoclonal antibody to ENA-78 and peptides identified through phage display that have high binding affinity to ENA-78.

Furthermore, using phage display, two peptides that recognize recombinant human CXCL5/ENA-78 were identified:

```
Peptide 1 (001418C, preferred peptide):
H-Pro-Val-Trp-Ala-his-leu-Asn-Pro-Pro-Trp-Leu-
Ala-NH2 (ALWPPNLHAWVP, SEQ ID NO: 1);

Peptide 2 (001417C, more preferred peptide):
H-Ile-Gly-Lys-Val-Asp-Ser-Asn-Ser-Val-Ser-
His-Ala-NH2 (AHSVSNSDVLGI, SEQ ID NO: 2).
```

Finally, it was found that chondrocyte conditioned medium promotes mitogentic signaling through PI3K/AKT pathway in MCF7A cells. As shown in FIGS. 5 and 6, chondrocyte conditioned medium exclusively induces proliferation in MCF7A and can be inhibited by LY294002 (PI3K inhibitor). A Western blot showed the activation of AKT and the ERK1/2 pathway in MCF7A upon treatment with AC CM. Finally, the inhibition of AC CM induced proliferation in MCF7A through PI3K.

The invention claimed is:

1. An in vitro method for identifying inhibitors of breast cancer metastasis, comprising the steps of:

a) providing a CXCL5 protein:

b) contacting in vitro said CXCL5 protein with at least one putative ligand of said CXCL5 protein in the presence of a peptide having the sequence of ALWPPNLHAWVP (SEQ ID NO: I) and/or a peptide having the sequence of AHSVSNSDVLGI (SEQ ID NO: 2), and wherein the at least one putative ligand competes for binding to the CXCL5 protein with one or both of the peptides of SEQ ID NO: 1 and SEQ ID NO: 2, and c) detecting in vitro a binding between said at least one putative ligand and said CXCL5 protein.

2. The method according to claim 1, further comprising the steps of:

d) in case of a binding of said putative ligand to said CXCL5 protein, detecting whether said binding between said putative ligand to said CXCL5 protein leads to a decrease of the migration and/or a re-differentiation of a breast cancer cell and/or a reduction of the number and/or size of breast cancer metastases.

3. The method according to claim 1, wherein said putative ligand is an inhibitor of the expression, stability and/or biological function of said CXCL5 protein.

4. The method, according to claim 2, wherein said breast cancer metastasis is a bone and/or lung metastasis.

5. The method, according to claim 3, wherein said putative ligand binds to the pocket of the CXCL5 protein.

* * * * *

SEQUENCE LISTING

```
<160> NUMBER OF SEQ ID NOS: 3

<210> SEQ ID NO 1
<211> LENGTH: 12
<212> TYPE: PRT
<213> ORGANISM: artificial sequence
<220> FEATURE:
<223> OTHER INFORMATION: peptide identified using phage display

<400> SEQUENCE: 1

Ala Leu Trp Pro Pro Asn Leu His Ala Trp Val Pro
1               5                   10


<210> SEQ ID NO 2
<211> LENGTH: 12
<212> TYPE: PRT
<213> ORGANISM: artificial sequence
<220> FEATURE:
<223> OTHER INFORMATION: peptide identified using phage display

<400> SEQUENCE: 2

Ala His Ser Val Ser Asn Ser Asp Val Leu Gly Ile
1               5                   10


<210> SEQ ID NO 3
<211> LENGTH: 114
<212> TYPE: PRT
<213> ORGANISM: homo sapiens

<400> SEQUENCE: 3

Met Ser Leu Leu Ser Ser Arg Ala Ala Arg Val Pro Gly Pro Ser Ser
1               5                   10                  15

Ser Leu Cys Ala Leu Leu Val Leu Leu Leu Leu Leu Thr Gln Pro Gly
            20                  25                  30

Pro Ile Ala Ser Ala Gly Pro Ala Ala Ala Val Leu Arg Glu Leu Arg
        35                  40                  45
```

-continued

```
Cys Val Cys Leu Gln Thr Thr Gln Gly Val His Pro Lys Met Ile Ser
    50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                85                  90                  95

Pro Phe Leu Lys Lys Val Ile Gln Lys Ile Leu Asp Gly Gly Asn Lys
            100                 105                 110

Glu Asn
```